United States Patent [19]

Mueller

[11] Patent Number: 4,681,845

[45] Date of Patent: Jul. 21, 1987

[54] INCREASED GLUCOSE LEVELS IN STARCH SACCHARIFICATION USING IMMOBILIZED AMYLOGLUCOSIDASE

[75] Inventor: William H. Mueller, Darien, Ill.

[73] Assignee: UOP Inc., Des Plaines, Ill.

[21] Appl. No.: 766,328

[22] Filed: Aug. 16, 1985

[51] Int. Cl.$^4$ .............................................. C12P 19/20
[52] U.S. Cl. ...................................... 435/96; 435/819
[58] Field of Search ..................................... 435/96, 94

[56] References Cited

U.S. PATENT DOCUMENTS

| 4,141,857 | 2/1979 | Levy | 252/430 |
| 4,511,654 | 4/1985 | Rohrbach et al. | 435/95 |
| 4,594,322 | 6/1986 | Thompson et al. | 435/95 |

FOREIGN PATENT DOCUMENTS 2129806  5/1984  United Kingdom .................. 435/96

Primary Examiner—Lionel M. Shapiro
Attorney, Agent, or Firm—Thomas K. McBride; John F. Spears, Jr.; Eugene I. Snyder

[57] ABSTRACT

Using an aged IMAG in series with fresh IMAG affords a saccharification product containing increased yields of glucose. In particular, using such a combination it is possible to obtain a product containing glucose at levels of at least about 94.0%. Such a process is readily adaptable to present industrial processes requiring glucose levels of at least 94.0%.

8 Claims, No Drawings

INCREASED GLUCOSE LEVELS IN STARCH SACCHARIFICATION USING IMMOBILIZED AMYLOGLUCOSIDASE

BACKGROUND OF THE INVENTION

Amyloglucosidase (AG) finds broad commercial use in the conversion of partially hydrolyzed starch, or thinned starch, to glucose. Processes for glucose production most often use soluble AG in a batch mode. Although the use of an immobilized AG (IMAG) has many desirable features, the maximum glucose levels ($G_{max}$) attainable using an IMAG are lower than those routinely available in processes using soluble AG. This limitation in $G_{max}$ is a severe handicap which has sharply curtailed the commercial development of IMAG. For example, many commercial processes are geared to a glucose level of at least 94.0% in the starch saccharification product, and product with glucose levels of even several tenths of a percent under that is unsuitable.

The lower $G_{max}$ attained when using IMAG appears to result from pore diffusion effects. In particular, it is believed that glucose which is formed in the smaller pores of an IMAG tends to have a longer residence time in an AG environment because of slow diffusion than does glucose which is formed in the larger pores of the support matrix. Since AG also catalyzes the irreverisble formation of a reversion product, isomaltose, the retention of glucose in the smaller pores leads to increased reversion product and a decreased $G_{max}$. The bitterness of isomaltose further exacerbates the effects of slow pore diffusion since glucose syrup often is used for its sweetness properties.

The invention herein is based on the surprising discovery that maximum glucose levels attained with aged IMAG are about 1% higher than those attained with fresh IMAG. The origin of this phenomenon is not known with certainty, but it is believed to arise from the lower reaction rate in aged IMAG, which lessens the effect of pore diffusion resistance, thereby allowing a higher $G_{max}$. That is, that glucose may have a longer residence time in an AG environment because of slow diffusion becomes less important as the reaction rate with the AG decreases. However uncertain may be the cause of a higher $G_{max}$, the fact of a higher $G_{max}$ from aged IMAG is beyond cavil.

SUMMARY OF THE INVENTION

The purpose of this invention is to increase the maximum glucose levels attained in the saccharification of thinned starch when using an immobilized amyloglucosidase. An embodiment is a method for saccharification of thinned starch where the IMAG consists of a fresh and aged IMAG in series, where the thinned starch feedstock first contacts the fresh IMAG and the saccharification product therefrom then contacts the aged IMAG. In a more specific embodiment the amyloglucosidase is immobilized on a support matrix comprising a porous refractory inorganic oxide impregnated with a polyamine subsequently crosslinked with an excess of a bifunctional reagent so as to afford a multiplicity of pendant functional groups. In a more specific embodiment the IMAG is an amyloglucosidase covalently bound to the aldehyde groups of a support matrix consisting of an alumina impregnated with polyethylenimine crosslinked with an excess of glutaraldehyde so as to afford pendant aldehydic groups. In yet another embodiment the ratio of aged to fresh IMAG is from about 95:5 to about 34:66.

DESCRIPTION OF THE INVENTION

It is an industrial fact of life that processes utilizing glucose as the saccharification product of thinned starch require a product containing at least about 94.0% glucose. The basis for this minimum glucose content arises from the fact that soluble AG routinely affords at least 94.0% glucose. However, the use of an immobilized amyloglucosidase almost invariably leads to glucose levels under 94.0%, and consequently its use has been severely curtailed in industry. This invention is a process of saccharifying starch to give glucose at levels of 94.0% and higher by using fresh and aged IMAG in series, with the thinned starch feedstock first contacting the fresh IMAG, and the saccharified product therefrom then being further hydrolyzed by the aged IMAG.

The feedstock used in this invention is a partially hydrolyzed, or thinned, starch solution. For the purpose of this application, thinned starch or partially hydrolyzed starch is a partially degraded starch containing a minor proportion of monosaccharides, up to about 10% but generally less than about 4%, and a distribution of polysaccharides, where from about 20% to about 70% are present as disaccharides through heptasaccharides, with from about 30% to about 80% present as higher molecular weight polysaccharides. The solids content varies with commercial users, but typically is in the range from about 25% to about 35% dry solids.

The feedstock of thinned starch is then contacted with fresh immobilized amyloglucosidase, and the product resulting therefrom is then contacted with aged IMAG, the contacting in both instances being under saccharification conditions. By "aged" IMAG is meant a product which already has been through at least one half-life. That is, an "aged" IMAG has an enzymatic activity which is not more than one-half of its initial enzymatic activity under identical conditions. The IMAG used can be even more "aged" than that, i.e., its activity may correspond to that after several half-lives, but it is not practical to use aged IMAG which has gone through more than about four half-lives. By "fresh" IMAG is meant a product which has been used less than one half-life.

The ratio of aged to fresh IMAG can vary over wide limits. Combinations from about 34:66 to about 95:5 produce increased maximum glcuose levels compared to those from fresh IMAG only, with ratios from about 80:2: to about 50:50 being most desirable. The above ratios refer to a situation where the initial activity of the aged IMAG is comparable to that of the fresh IMAG. Under any set of experimental conditions the contact time of the feedstock and ratio of aged to fresh IMAG will be chosen to afford a final product containing at least about 94.0% glucose.

The source of amyloglucosidase is not at all critical and it is believed that any AG may be used in the practice of this invention. Similarly, the process which is our invention may be used with any porous support matrix which effectively immobilizes AG. A particularly preferred support matrix is that described in U.S. Pat. No. 4,141,857, but it needs to be stressed that the invention herein is applicable to IMAG generically.

The temperature at which the enzymatic hydrolysis is conducted depends upon the thermostability of the enzyme used, but generally the temperature is between about 40° and about 80° C., with a temperature of about 55° C. being the most usual one. However, it is to be understood that if the AG is sufficiently thermostable to allow the process to be run at a higher temperature, such a temperature is contemplated to be within the saccharification conditions for the purpose of this invention. The pH at which hydrolysis is effected normally is in the range from about 3 to about 8, with a range between about 4 to about 5 being generally most desirable. It is to be understood that the optimum pH range may depend upon the particular source of AG and its determination is well within the capabilities of one skilled in the art.

Many variants of the process herein can be constructed. The only requirement is that the thinned starch feedstock first come into contact with fresh IMAG, where the major part of saccharification occurs, and the product therefrom then come into contact with aged IMAG, where the remainder of the hydrolysis occur. In one variant both the fresh and aged IMAG are loaded into the same reactor with the fresh IMAG occupying the front end, or initial section, of the reactor. In another variant, which is a preferred mode of operation, the reactor is continually topped off with fresh IMAG. In this variant the ratio of fresh to aged IMAG is initially relatively high, but as glucose production proceeds and fresh IMAG is needed to maintain an approximately constant liquid hourly space velocity the ratio of fresh to aged IMAG continually decreases. This replenishment variation may be continued to be practiced until the reactor has been so filled with IMAG that it is impractical to load additional IMAG.

In another variant there can be two or more reactors in series, the initial one(s) containing fresh IMAG and the latter one(s) containing aged IMAG. It will be appreciated that only two reactors are needed for the practice of this invention, but more than two reactors in series may be used although such an arrangement is not necessarily beneficial.

The following examples are merely illustrative of my invention which is not to be limited thereby in any way.

EXAMPLE 1

The support matrix was prepared generally as described in U.S. Pat. No. 4,141,857. In a typical preparation 100 ml of porous alumina particles were impregnated with 13.5 mg polyethylenimine (PEI) per g alumina by contacting the latter with a 3.2% aqueous solution of PEI and slowly evaporating the water at about 80° C. at atmospheric pressure over a period of approximately 4 hours. The PEI was then reacted with excess of an aqueous solution of glutaralehyde in an amount of about 0.12 g per g PEI-alumina. Excess adhering but unreacted glutaraldehyde was removed by washing the solid with copious quantities of water.

Immobilized IMAG was prepared by contacting the support matrix as prepared above with an aqueous solution of AG (50 units/ml) at pH ca. 4 and at ambient temperature for a period of about 15 hours. Excess enzyme solution was removed by decantation, and adhering but unbound AG was removed by washing the solid with copious quantities of an aqueous solution of 30 wt.% Maltrin 150.

A jacketed reactor maintained at 55° C. was loaded with 20 ml of the IMAG prepared above, and a feedstock of 30 wt.% thinned starch (available commercially as Maltrin 150, DE15-18) at pH 4.5 and containing 1000 ppm sulfite as $Na_2SO_3$ was passed over the fixed bed in a plug flow. A maximum product glucose level of 92.9 wt.% was obtained initially at a flow rate of 70 ml/hr. The feedstock flow was adjusted to maintain the effluent at a minimum 92 wt.% glucose. After 60 days the flow rate was about 40 ml/hr.

At this time 10 ml of fresh IMAG, prepared as described above, was placed in a separate jacketed reactor preceding the one containing the aged IMAG, and feedstock was passed through both reactors in series in a plug flow. A maximum product glucose level of 94.0 wt.% was obtained at a flow rate of 57 ml/hr.

EXAMPLE 2

Within 48 hours of completing the test of fresh/aged IMAG in Example 1, a second test was commenced using the same fresh and aged IMAG in the same quantities and flow configuration. In the second test, the feedstock to the fresh/aged IMAG consisted of 27 wt.% Maltrin 150 in aqueous solution at pH 4.5 and containing 1000 ppm sulfite as $Na_2SO_3$. When this feed was passed through the combined 30 mls of fresh and aged IMAG maintained at 55° C., a maximum product glucose level of 94.6 wt.% was obtained at a flow rate of 57 ml/hr. This demonstrates that beneficial effects also can be obtained using a feedstock at a lower level of dry solids. The results also suggest that a somewhat higher glucose level is obtained from a feedstock of lower dry solids.

What is claimed is:

1. A method of converting a partially hydrolyzed starch solution to glucose comprising contacting under saccharifying conditions a feedstock of said starch solution with a first portion of a fresh immobilized amyloglucosidase which has been used for less than one half-life followed by contacting under saccharification conditions the resulting hydrolyzed product with a second portion of an aged immobilized amyloglucosidase which has been used for more than one half-life, said first and second portions being in series with the contact times and ratio of aged to fresh immobilized amyloglucosidase sufficient to afford a product containing at least about 94.0% glucose, and recovering the glucose formed thereby.

2. The method of claim 1 where the fresh and aged immobilized amyloglucosidase are in different reaction zones of the same reactor.

3. The method of claim 1 where the fresh and aged immobilized amyloglucosidase are in different reactors.

4. The method of claim 1 where saccharification conditions include a temperature between about 40° and about 80° C.

5. The method of claim 1 wherein saccharification conditions include a pH between about 3 to about 8.

6. The method of claim 1 where the pH is between about 4 to about 5.

7. The method of claim 1 where the ratio of aged to fresh immobilized amyloglucosidase is from about 95:5 to about 34:66.

8. The method of claim 7 where the ratio of aged to fresh immobilized amyloglucosidase is from about 80:20 to about 50:50.

* * * * *